United States Patent [19]
Ryan et al.

[11] Patent Number: 5,810,835
[45] Date of Patent: Sep. 22, 1998

[54] CATHETER INSERTION DEVICE WITH VALVE

[75] Inventors: Enda B. Ryan; Brendan J. Duggan, both of Sligo, Ireland

[73] Assignee: Abbott Laboratories, Abbott Park, Ill.

[21] Appl. No.: 733,900

[22] Filed: Oct. 18, 1996

Related U.S. Application Data

[63] Continuation of Ser. No. 365,398, Dec. 28, 1994, abandoned.

[51] Int. Cl.$^6$ .................................................. A61F 11/00
[52] U.S. Cl. ........................... 606/108; 604/159; 604/280
[58] Field of Search .................................. 606/108, 205; 604/159, 167, 169, 237, 280

[56] References Cited

U.S. PATENT DOCUMENTS

| | | | |
|---|---|---|---|
| 3,995,628 | 12/1976 | Gula et al. . | |
| 4,342,313 | 8/1982 | Chittenden | 604/159 |
| 4,857,062 | 8/1989 | Russell | 604/256 |
| 5,176,650 | 1/1993 | Haining . | |
| 5,300,032 | 4/1994 | Hibbs et al. . | |
| 5,304,142 | 4/1994 | Liebl et al. | 604/167 |

FOREIGN PATENT DOCUMENTS

| | | |
|---|---|---|
| 0370721 | 5/1990 | United Kingdom . |
| WO 90/03196 | 4/1990 | WIPO . |
| WO 93/13822 | 7/1993 | WIPO . |

*Primary Examiner*—Michael Buiz
*Assistant Examiner*—Patrick W. Rasche
*Attorney, Agent, or Firm*—David C. Hannum

[57] ABSTRACT

The catheter insertion device of the present invention includes a catheter dispenser having a catheter outlet extending from a base and a drum receptacle engaged to the base in a rotating relationship. An inlet opening in the base is coaxially aligned with the catheter outlet. A passageway extends from the inlet opening tangentially through the catheter drum to the catheter outlet. A rigid needle is disposed through the passageway so that the sharp tip extends beyond the catheter outlet. A flexible introducer catheter generally contiguously and telescopically surrounds the distal portion of the needle. The introducer catheter extends beyond the catheter outlet to a position on the needle that is proximate to the sharp tip and is operatively associated with the needle for insertion into the vein of a patient. A one way flow valve is in fluid-tight connection with the proximal end of the flexible introducer catheter. The valve forms a portion of the passageway so that when the needle is slidably removed from the passageway the valve minimizes the fluid backflow from the vein. When the catheter drum is rotated relative to the base, the drum catheter is threadably inserted into and through the one way valve, through the indwelling flexible introducer catheter and into the vein of the patient.

1 Claim, 2 Drawing Sheets

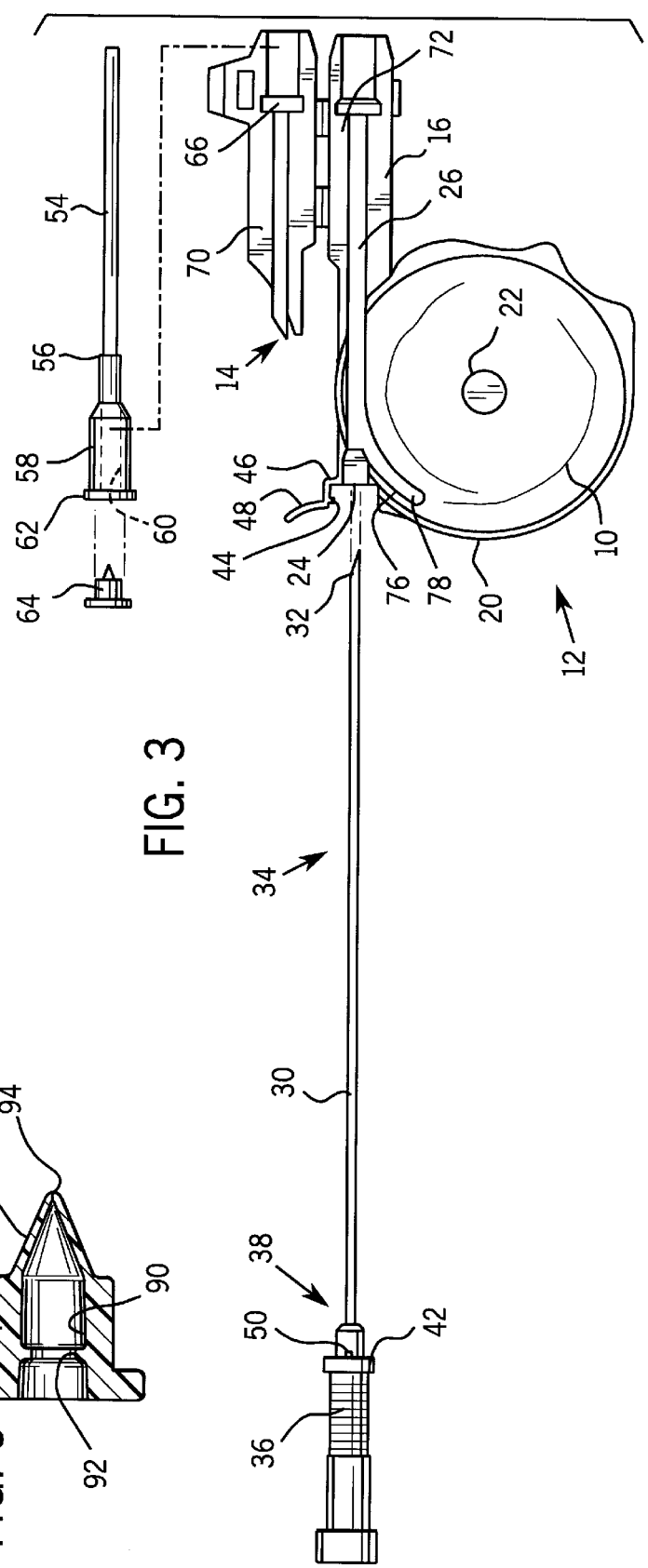

CATHETER INSERTION DEVICE WITH VALVE

This application is a continuation of U.S. patent application Ser. No. 08/365,398 filed Dec. 28, 1994 now abandoned.

FIELD OF THE INVENTION

The present invention relates generally to an insertion device used to introduce a catheter into a vein of a patient and more particularly to an insertion device for storing and advancing a long flexible catheter into the vein of the patient while maintaining the aseptic condition of the catheter and minimizing the blood leakage due to the venipuncture procedure.

BACKGROUND OF THE INVENTION

For many medical procedures, such as intravenous fluid administration, communication with the blood system of a patient is required. Ordinarily it is necessary to use an incising element such as a rigid needle having a sharp tip to gain access to a vein. However, it is not desirable to leave a sharp needle in place in the vein for any extended period of time due to the potential damage the sharp tip may cause. Thus a flexible conduit such as a plastic catheter is often inserted into the vein concurrently with the rigid needle. Since the flexible plastic catheter is concentrically positioned over (or alternately within) the rigid needle, the needle can then be withdrawn leaving only the flexible catheter indwelling in the vein. Abbocath® Catheters, manufactured and sold by Abbott Laboratories are examples of indwelling intravenous catheters having a flexible catheter over a rigid, withdrawable needle. The Abbocath-T® Catheter, for example, is widely used for venipuncture.

Introducing a longer catheter such as a flexible catheter suitable for central venous monitoring or catherization has additional complications. These long, flexible catheters are typically compactly stored and dispensed from a rotatable drum cartridge since the long catheter is easily contaminated and difficult to advance into the vein. An example of such a drum cartridge device is described in U.S. Pat. No. 3,561, 445 entitled "Catheter placement Unit." The long flexible catheter stored in the drum is inserted through a metal needle without exposing the catheter. However, a concern when using a catheter-through-needle device is the possibility of severing or puncturing the catheter with the sharp heel of the needle if the catheter is inadvertently withdrawn back through the needle.

Alternatively, a long catheter from a drum cartridge can be inserted through a flexible introducer catheter rather than through a metal needle. The flexible introducer catheter is implanted by using a rigid needle concentrically positioned inside the flexible introducer catheter. The rigid needle is then removed leaving only the flexible introducer catheter indwelling in the patient. An example of a catheter-through-catheter (i.e. flexible introducer) device is described in U.S. Pat. No. 4,342,313 entitled "Catheter Insertion Device," the disclosure of which is hereby incorporated by reference in this application.

Referring now to FIG. 1 of the present drawings, a drum cartridge catheter-through-catheter dispensing and insertion device 13 according to U.S. Pat. No. 4,342,313 is shown. The device includes an elongated needle 31 disposed through the catheter dispenser from a tubular needle housing 25 to an opposite tubular catheter outlet 17. The flexible introducer catheter 55 has an inner diameter that concentrically and coaxially surrounds the outer diameter of the distal portion of the needle 31. The flexible introducer catheter extends generally from the catheter outlet 17 to the needle tip 33. The proximal end 57 of the flexible introducer catheter 55 has a flared socket 59 with an interference fit on the tubular catheter outlet 17. The flexible introducer catheter 55 is tapered at the distal end to allow the needle 31 and flexible introducer catheter 55 to be introduced into the vein of the patient without undue discomfort or injury.

Following venipuncture, the rigid needle 31 is slidably removed from the indwelling flexible introducer catheter 55 in the vein of the patient. Access to the vein is maintained by the indwelling flexible introducer catheter 55. The long flexible catheter 11 in the drum cartridge 21 may then be telescopically threaded into the catheter outlet 17 and advanced through the flexible introducer catheter 55 into the vein of the patient.

The drum cartridge includes a spindle 23 anchored to the base 15 to allow rotation of the drum relative to the base. The drum 21 is selectively detachable from base 15 in order to allow access to a fluid connector 19 at the end of the flexible drum catheter. Thus the long drum catheter 11 may be removed from dispenser 13 and fluidly connected after the desired length of the drum catheter 11 is inserted into the vein of the patient.

The drum catheter 11 is spirally wound within drum cartridge 21. A stylet 81 extends through the drum catheter urging the catheter against the drum wall so as to facilitate dispensing of the drum catheter 11. The tendency of the stylet 81 and drum catheter 11 to uncoil forces the catheter against the peripheral wall of the drum. Thus manual rotation of the drum 21 with respect to base 15 will force the coiled drum catheter 11 out of drum cartridge 21, through the tangential catheter outlet 17 and into the indwelling flexible introducer catheter 55.

However, one drawback of the above described catheter-through-catheter (i.e. flexible introducer) device is the potential for blood leakage since the indwelling flexible introducer catheter is open to the vein after the rigid needle 31 is withdrawn and before the drum catheter 11 is advanced into the vein. While the blood leakage during the transition does not pose any danger to the patient, the leakage from the open indwelling introducer catheter does create a mess from the blood that leaks from the open introducing catheter.

Therefore it is desirable in a catheter-through-catheter insertion device to minimize the blood leakage from the indwelling flexible introducer catheter during the transition (i.e. change over) from the rigid needle to the drum catheter.

It is also desirable to make the drum cartridge and catheter insertion device an integrally assembled unit that is compact in size and easy to use.

SUMMARY OF THE INVENTION

The present invention provides a catheter insertion device which includes a catheter dispenser having a base with a catheter outlet extending from the base. A drum cartridge catheter receptacle is engaged to the base in a rotating relationship. A needle inlet opening in the base is in coaxial alignment with the catheter outlet. A passageway extends from the inlet opening tangentially through the catheter drum to the catheter outlet. A venipuncture needle is disposed through the passageway so that a sharp needle tip extends beyond the catheter outlet for entering the vein of a patient. A needle hub at the proximal end of the needle is positioned in the inlet opening. A flexible introducer catheter member generally contiguously and telescopically surrounds the distal portion of the needle. The introducer catheter extends beyond the catheter outlet to a position on the needle that is proximate to the sharp tip. Thus the flexible introducer catheter is operatively associated with the needle for insertion into the vein of a patient.

A one way fluid flow valve is in fluid-tight connection with the proximal end of the flexible introducer catheter. The valve forms a portion of the passageway so that when the rigid needle is slidably removed from the passageway, the one way fluid flow valve minimizes the fluid backflow from the vein. When the catheter drum is rotated relative to the base, the drum catheter is threadably inserted into and through the one way fluid flow valve, through the indwelling flexible introducer catheter and into the vein of the patient.

Numerous other advantages and feature of the present invention will become readily apparent from the following description of the invention, the claims and the accompanying drawings.

BRIEF DESCRIPTION OF THE DRAWINGS

FIG. 3 of the drawings is an exploded side view of the catheter insertion device of FIG. 2;

FIG. 4 of the drawings is an enlarged top view of the fluid flow valve of the catheter insertion device of FIG. 3;

FIG. 5 of the drawings is a top cross section view of the fluid flow valve of FIG. 4;

FIG. 6 of the drawings is a vertical section of the fluid flow valve of FIG. 4; and FIG. 7 of the drawings is a front view of the fluid flow valve of FIG. 4.

DESCRIPTION OF THE PREFERRED EMBODIMENTS

While this invention is susceptible of embodiment in different forms, the specification and the accompanying drawings disclose one or more forms as examples of the invention. The invention is not intended to be limited to the embodiments described, the scope of the invention being pointed out in the appended claims.

Figure 1:
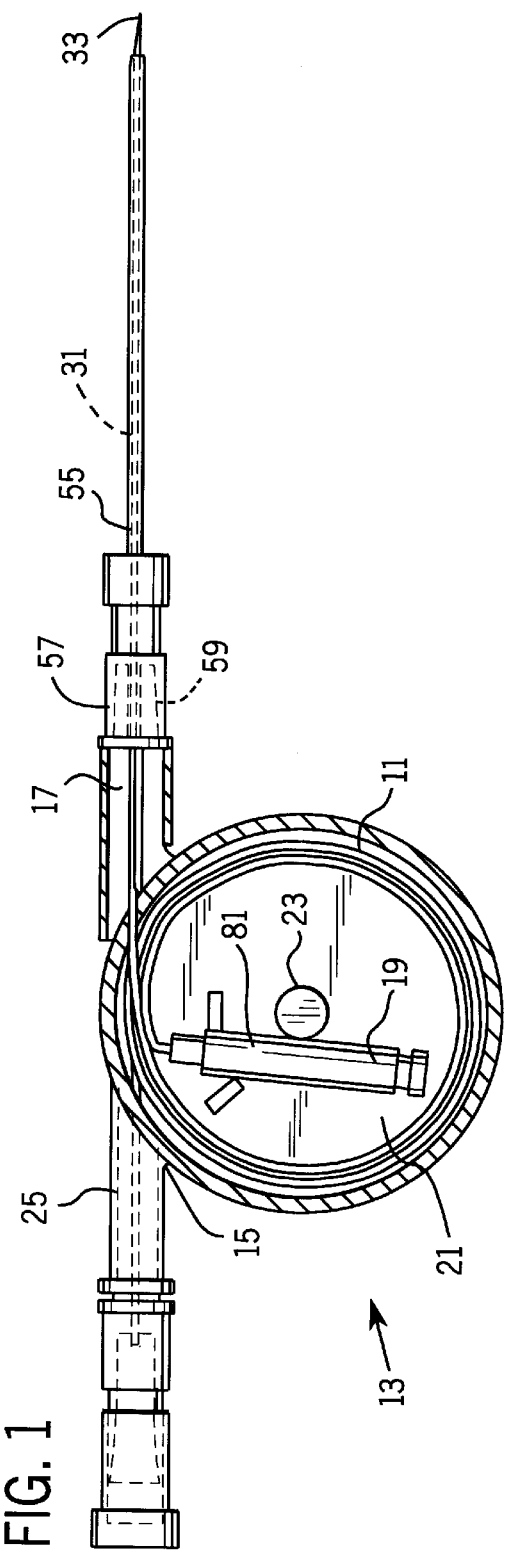
FIG. 1 of the drawings is a side view in partial section of a prior art catheter-through-catheter insertion device.
Figure 2:
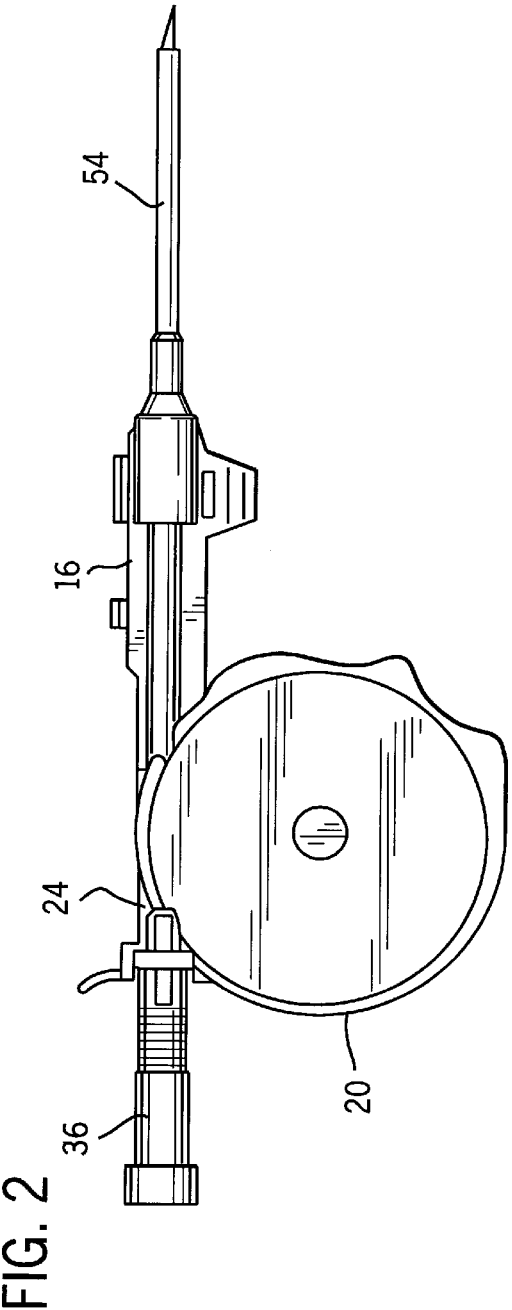
FIG. 2 of the drawings is a side view of the assembled catheter-through-catheter insertion device with a fluid flow valve according to the present invention.

The catheter insertion device of the present invention, as best understood with reference to FIGS. 2 and 3 includes a long flexible catheter 10 coiled within a catheter dispenser 12. The dispenser includes a base 14 having a tubular catheter outlet 16 extending tangentially from the base. A rotatable catheter drum 20 is connected to the base by a spindle 22 for rotation relative to the base. The flexible catheter 10 is wound internally within the drum and is mechanically engaged with drum 20 so that rotation of drum 20 relative to base 14 causes drum catheter 10 to be threadably moved through catheter outlet 16.

A needle inlet opening 24 is positioned in the base in alignment with the catheter outlet. A passageway 26 extends through the base from the inlet opening 24 to the catheter outlet 16. The passageway 26 is tangential to the catheter drum 20.

An elongated needle 30 having a sharp tip 32 at its distal end 34 is coaxially and slidably disposed through the passageway so that the sharp needle tip extends beyond catheter outlet 16. The needle tip is preferably beveled and the needle is orientated in the bevel up position suitable for venipuncture.

A needle hub member 36 is fixed to the proximal end 38 of needle 30 and has an exterior shape that can be easily grasped by the user to slidingly remove the needle from the needle inlet opening 24. The needle hub is constructed to include an engagable structure such as outward lip 42 for engaging with a small catch 44 associated with the inlet opening 24. A resilient flange 46 on the base extends parallel to the needle. The short catch 44 extends perpendicularly from the resilient flange 46 to engage the lip 42 of the needle hub 36.

A lever 48 extends perpendicular to the resilient flange and opposite to the catch 44 to allow the resilient flange 46 to be deflected to release the catch from the lip of the needle hub. The lever 48 is readily activated by a finger of the user to facilitate the easy removal of the hub 36 and needle 30 from catheter dispenser 12.

The needle hub 36 also includes a single forward extending prong 50 that mates with an open portion at the inlet opening 24 of the dispenser 12 so as to correctly orientate the needle tip 32 in the bevel up position.

A flexible introducer catheter member 54 such as a thin plastic catheter continuously and telescopically surrounds the distal portion 34 of needle 30. Flexible introducer catheter 54 extends forward on the needle, but does not extend over the sharp needle tip 32 in order to facilitate venipuncture by the concentrically combined needle 30 and flexible introducer catheter 54.

After venipuncture flashback is observed in the needle hub 36, the needle 30 is slidably removed from the flexible introducer catheter 54 through the passageway 26 and the inlet opening 24. Since flexible introducer catheter 54 is constructed of a flexible, resilient material, once needle 30 is removed, the danger of injury to the vein is reduced. Clockwise rotation of the drum 20 threads catheter 10 through catheter outlet 16 into flexible introducer catheter 54 and hence into the vein of the patient.

The proximal end 56 of flexible introducer catheter 54 includes a socket 58 with an axial bore 60 extending longitudinally through the socket and a socket rim 62 at the proximal end of the socket. Socket 58 is fixed in fluid-tight connection to flexible introducer catheter 54 and a one way fluid flow valve 64 is insert into the axial bore 60 of the socket to abut the socket rim 62. The one way fluid flow valve 64 is normally closed and thus closes the bore of the flexible introducer catheter 54 unless the needle 30 or drum catheter 10 is in the bore.

Catheter outlet 16 is preferably a tubular construction connected to base 14 and tangential to the drum 20. The socket 58 is engaged in a hollow cavity 66 in the catheter outlet 16. The cavity 66 has a size and shape similar to the socket 58, and thus holds the socket securely in the catheter outlet 16.

As best seen in FIG. 3, catheter outlet 16 includes a hinged section for securably engaging socket 58 in the hollow cavity 66. Upper portion 70 and lower portion 72 of tubular catheter outlet member 16 are in hinged relation to each other, by use of a resilient, flexible material so that catheter outlet 16 may be selectively openable as required.

The base 14 includes an integrally molded passage 76 including a first end 78 in parallel curvature to the periphery of drum 20 and a second end extending tangentially into the passageway 26 from the drum 20. The passage 76 holds the lead end of the drum catheter so as to readily guide the drum catheter 10 out of the drum 20 and into the one way fluid flow valve 64 and flexible introducer catheter 54. When the drum 20 is separated from the base 14, the drum catheter 10 is removed from base 14 due to the open passage 76..

As best seen with reference to FIGS. 4–7, the one way fluid flow valve 64 is molded of a resilient plastic material in a generally cylindrical shape. When the valve is assembled in the socket 58, the outer diameter 84 of the valve has an interference fit with the bore 60 of the socket 58. The valve lip 86 abuts against the socket lip 62 to locate the valve at the proximal end of the flexible introducer catheter 54. A duckbill valve configuration is preferred.

The one way fluid flow valve 64 has an inner surface 90 with a general inner diameter. The inner diameter of the valve inner surface 90 allows the outer diameter of the needle 30 to fit through the valve. Likewise, the width of the slot 94 at the distal end of the valve is constructed to accommodate the outer diameter of the needle 30.

Valve 64 also includes a circumferential wiper 92 projecting radially inward on the inner surface. The wiper has an inner diameter so as to seal around the drum catheter 10 when the drum catheter is inserted into the one way fluid valve 64 and through the flexible introducer cannula 54. Since the integral wiper is made of the same resilient material as the valve 64, the annular wiper 92 bends out of the way when the larger outer diameter of the flexible introducer cannula 54 is inserted through the valve.

The angled face sections 96 of the one way fluid flow valve converge at slot 94 so that fluid backpressure from the vein due to the open indwelling flexible introducer catheter 54 closes the face sections 96 and slot 94 when the needle 30 or the drum catheter 10 is not in the flexible introducer catheter.

The various components of the catheter dispenser 12 are preferably molded from plastics such as polyethylene, polypropylene or an equivalent medical grade plastic. The plastics should preferably be medical grade and sterilizable. Translucent or transparent plastic would allow observation of the length of catheter 10 remaining in drum 20. The flexible introducer catheter 54 is preferably made of a flexible plastic material such as Teflon®. The drum catheter 10 may be constructed of polyvinyl chloride or preferably polyurethane. Needle 30 and stylet 80 are manufactured of a suitable rigid material such as stainless steel. The one way fluid flow valve 64 is molded of a sterilizable silicone elastomer material.

The catheter insertion device with a backflow valve according to the present invention is used as follows. The combined needle 30 and flexible introducer catheter 54 are inserted into a patient's vein in a venipuncture procedure. Needle 30 is then grasped at hub 36 and removed from the dispenser passageway, leaving the flexible introducer catheter indwelling in the vein. The one way fluid flow valve 64 in the flexible introducer catheter 54 minimizes any backflow of blood from the vein through the flexible introducer catheter. Clockwise rotation of drum 20 causes catheter 10 to be advanced through the catheter outlet 16, the one way fluid flow valve 64, and the flexible introducer catheter 54 into the vein of the patient. When the end of the flexible drum catheter 10 is in the proper position, the drum 20 is snapped apart from base 14. The hinged portions 70 and 72 of the catheter outlet 16 are then opened and socket 58 as well as the introducer catheter 54 are removed from the hollow cavity 66 and catheter outlet 16. The drum catheter 10 may then be entirely separated from the base 14, and the base is discarded. The flexible introducer catheter 54 is then withdrawn from the venipuncture site and slid to an out of the way position, near hub 36 for example, on the unwound drum catheter 10. Thus in the final configuration only the drum catheter 10 remains indwelling in the patient at the venipuncture site. Furthermore, the blood leakage from the vein through the flexible introducer catheter 54 is minimized during the transition from the withdrawal of the rigid needle 30 to the insertion of the drum catheter 10.

It will be readily apparent from the foregoing detailed description of the invention and from the illustrations thereof that numerous variations and modifications may be effected without departing from the true spirit and scope of the novel concepts or principles of this invention.

What is claimed is:

1. A catheter insertion device comprising:

a catheter dispenser having a base, a catheter outlet extending from the base, and a rotatable catheter drum rotatably mounted on the base, a catheter mounted on said rotatable catheter drum, said catheter drum constructed so that rotation of said catheter drum relative to said base moves said catheter laterally through said catheter outlet;

an inlet opening in said catheter dispenser in coaxial alignment with said catheter outlet;

said catheter dispenser defining a passageway extending from said inlet opening to said catheter outlet;

a needle having a proximal end portion and a distal end portion, a sharpened tip for insertion into a vein of a patient mounted on said distal end portion, said needle constructed to slide through said passageway so that said sharpened tip extends beyond said catheter outlet;

a flexible introducer catheter member constructed to substantially concentrically surround a portion of said distal end portion of said needle, said flexible introducer catheter member constructed to substantially concentrically surround a portion of said catheter when said drum catheter advances said catheter through said catheter outlet, a portion of said flexible introducer catheter extending beyond said catheter outlet, a one-way flow valve disposed within said flexible introducer catheter, said one-way flow valve constructed to minimize backflow of fluid through said flexible introducer catheter when said needle and said catheter are withdrawn therefrom, said one-way flow valve constructed such that said needle and said catheter are slidable therethrough, said flexible introducer catheter member further including a wiper means for substantially fluidly sealing against said flexible introducer catheter member upon disposition of said catheter through said wiper, without necessitating the imposition of axial compressive forces on said wiper in order to effect the seal, said wiper projecting radially inwardly from an interior wall of said flexible introducer catheter, said wiper means disposed within said catheter member and constructed such that said needle and said catheter are slidable therethrough.

* * * * *